(12) United States Patent
Shin et al.

(10) Patent No.: US 11,878,984 B2
(45) Date of Patent: Jan. 23, 2024

(54) **COMPOUNDS DERIVED FROM *STREPTOMYCES* AND USES THEREOF**

(71) Applicant: KOREA INSTITUTE OF OCEAN SCIENCE & TECHNOLOGY, Busan (KR)

(72) Inventors: Hee Jae Shin, Busan (KR); Byeoung Kyu Choi, Daegu (KR); Hwa Sun Lee, Busan (KR); Hyi Seung Lee, Busan (KR); Yeon Ju Lee, Busan (KR); Jong Seok Lee, Busan (KR); Ji Hoon Lee, Busan (KR)

(73) Assignee: KOREA INSTITUTE OF OCEAN SCIENCE & TECHNOLOGY, Busan (KR)

( * ) Notice: Subject to any disclaimer, the term of this patent is extended or adjusted under 35 U.S.C. 154(b) by 153 days.

(21) Appl. No.: 17/274,988

(22) PCT Filed: Jun. 3, 2019

(86) PCT No.: PCT/KR2019/006660
§ 371 (c)(1),
(2) Date: Mar. 10, 2021

(87) PCT Pub. No.: WO2020/054946
PCT Pub. Date: Mar. 19, 2020

(65) Prior Publication Data
US 2022/0033413 A1 Feb. 3, 2022

(30) Foreign Application Priority Data
Sep. 11, 2018 (KR) .................... 10-2018-0108327

(51) Int. Cl.
*A61K 31/35* (2006.01)
*A61P 25/28* (2006.01)
*C07D 493/16* (2006.01)

(52) U.S. Cl.
CPC ............ *C07D 493/16* (2013.01); *A61K 31/35* (2013.01); *A61P 25/28* (2018.01); *C07B 2200/07* (2013.01)

(58) Field of Classification Search
CPC .......................... C07D 492/16; C07D 493/16
See application file for complete search history.

(56) References Cited

FOREIGN PATENT DOCUMENTS

| KR | 10-2007-0026454 A | 3/2007 |
|---|---|---|
| KR | 1020080042888 A | 5/2008 |

OTHER PUBLICATIONS

Yuste, J. E. et al. "Implications of glial nitric oxide in neurodegenerative diseases." Front. Cell. Neurosci. (2015), 9, pp. 1-13. (doi: 10.3389/fncel.2015.00322).*
International Search Report for International Patent Application No. PCT/KR2019/006660 dated Aug. 30, 2019 (7 pages).
Jing et al., "Diocollettines A, an unusual tricyclic diarylheptanoid derivative from the rhizomes of Dioscorea collettii", Tetrahedron Letters, vol. 57, No. 29, (2016) pp. 3215-3217.
Zhang et al., "Thermal behavior and thermal safety of 6bnitrohexahydro-2H-1,3,5-trioxacyclopenta[cd]- pentalene-2,4,6-triyltrinitrate", RSC Advances, vol. 7, No. 49, (2017), pp. 30747-30754.
Choi et al., "Streptoglycerides A-D with a Rare 6/5/5 Tricyclic Ring Skeleton from a Marine Actinomycete Streptomyces species", Organic Letters, vol. 20, No. 19, (2018), pp. 6037-6040.

* cited by examiner

*Primary Examiner* — Susanna Moore
(74) *Attorney, Agent, or Firm* — Foley & Lardner LLP

(57) ABSTRACT

The present invention relates to new compounds derived from marine actinomycetes *Streptomyces*, and the new compound according to the present invention has an inhibitory effect of NO production on BV-2 microglia stimulated with LPS, and thus can be utilized for the prevention and treatment of neuroinflammatory diseases.

5 Claims, 10 Drawing Sheets

$^1H \equiv\!\!\equiv ^1H$ gCOSY $^1H \frown ^{13}C$ gHMBC

COMPOUNDS DERIVED FROM *STREPTOMYCES* AND USES THEREOF

CROSS-REFERENCE TO RELATED APPLICATIONS

This application is a U.S. National Phase Application under 35 U.S.C. § 371 of International Application No. PCT/KR2019/006660, filed on Jun. 3, 2019, which claims the benefit of priority to KR 10-2018-0108327, filed on Sep. 11, 2018, both of which are incorporated herein by reference in their entirety.

TECHNICAL FIELD

The present invention relates to new compounds derived from *Streptomyces* and a use thereof.

BACKGROUND ART

Recently, researches on new secondary metabolites from marine resources, especially from marine biological resources are getting more and more attention as the new secondary metabolites with various chemical structures can be utilized as lead compounds for the treatment of human diseases. Among the marine biological resources, actinomycetes have been known as an important supply source for natural products with biological activities. Particularly, a substantial proportion of natural products having biological activities produced from microorganisms has been found to be produced by *Streptomyces* sp.

The genus *Streptomyces* includes aerobic gram-positive bacteria that produce a branched mycelium, and the produced mycelium forms a substrate mycelium with a complex structure. The genus *Streptomyces* is famous for unique and complicated secondary metabolism, and natural products derived from this process have been researched for a wide range of biological activities such as antibacterial, antiviral, anticancer, antihypertension, antibiotics, and immunosuppressive activities. Since Selman Waksman first discovered streptomycin in 1952 from metabolites of *Streptomyces griseus* of the soil, although various antibiotics such as aureomycin derived from *Streptomyces aureofaciens*, blasticidin S derived from *Streptomyces griseochromogenes*, and polyoxin derived from *Streptomyces asoensis* have been discovered and separated, and have been produced on an industrial scale through culturing of *Streptomyces*, a lot of research is being under way as new secondary metabolites that have not been discovered yet in addition to the known antibiotics are believed to exist.

Microglial cells are macrophages in the brain that exhibit immune responses to brain damage or infection. However, uncontrolled and excessive activation of microglia often contributes to inflammation-mediated neurodegeneration. Therefore, the suppression of pro-inflammatory mediators in activated microglia may lead the development of therapeutic agents for various neuronal diseases.

DISCLOSURE

Technical Problem

An object of the present invention is to provide new secondary metabolites isolated from marine actinomycetes *Streptomyces*.

Furthermore, the other object of the present invention is to provide new compounds for the prevention or treatment of neurodegenerative diseases.

Technical Solution

The present invention provides new compounds of the following Chemical Formula 1 produced from a *Streptomyces* strain isolated from a mangrove sample collected in Kosrae Island.

[Chemical Formula 1]

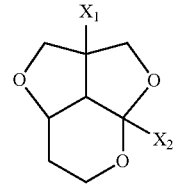

in Chemical Formula 1, $X_1$ is H or OR;
R is H or —Y—Z;
Y is carbonyl, amido or amide, or $C_1$-$C_6$ alkyl or alkylene;
Z does not exist, or $C_5$-$C_{10}$ substituted or unsubstituted aryl;
a substituent of the aryl is one or more selected from the group consisting of a hydroxy group, and $C_1$-$C_6$ alkyl and amino groups when the aryl is substituted; and
$X_2$ is $C_3$-$C_{12}$ saturated or unsaturated linear or branched alkyl, or $C_3$-$C_{12}$ alkenyl.

Advantageous Effects

Compounds represented by Chemical Formula 1 according to the present invention, an optical isomer or a pharmaceutically acceptable salt thereof may be used in the prevention and treatment of neurodegenerative diseases by inhibiting the production of NO in microglial cells and controlling neuroinflammation-related factors.

MODES OF THE INVENTION

Compound of Chemical Formula 1

Figure 1A:
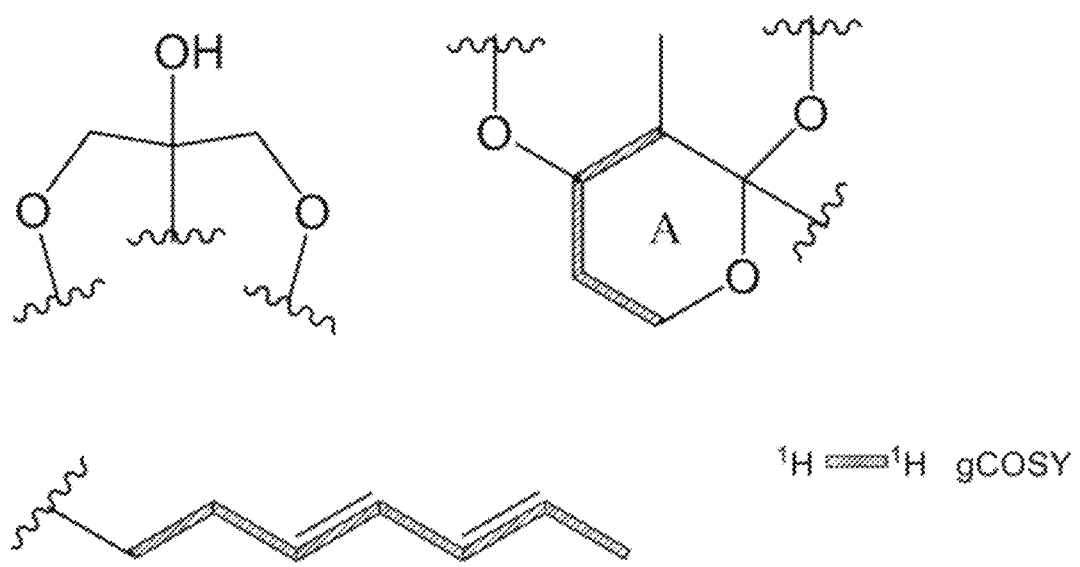
FIG. 1a illustrates COSY correlations (dashed line) with a partial structure of compound 1.
Figure 1B:
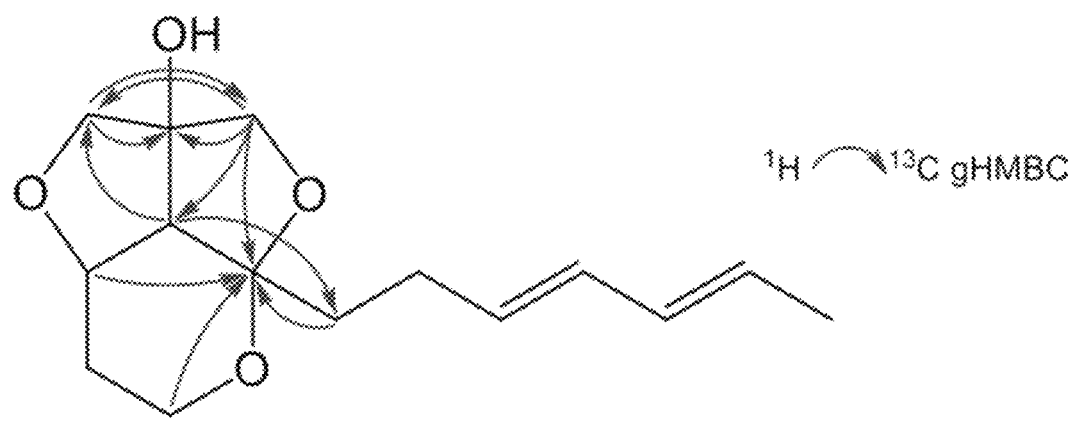
FIG. 1b illustrates HMBC correlations (solid line) of compound 1.

The present invention relates to compounds represented by the following Chemical Formula 1, an optical isomer or a pharmaceutically acceptable salt thereof.

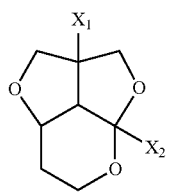

[Chemial Formula 1]

in Chemical Formula 1, $X_1$ may be H or OR; R may be H or —Y—Z;

Y may be carbonyl, amido or amide, or $C_1$-$C_6$ alkyl or alkylene;

Z may not exist, or may be $C_5$-$C_{10}$ substituted or unsubstituted aryl;

herein, a substituent of the aryl when the aryl is substituted may be one or more selected from the group consisting of a hydroxy group, and $C_1$-$C_6$ alkyl and amino groups; and $X_2$ may be $C_3$-$C_{12}$ saturated or unsaturated linear or branched alkyl, or $C_3$-$C_{12}$ alkenyl.

The aryl may be selected from the group consisting of phenyl, tolyl, xylenyl, naphthyl, and hydroxyphenyl. Here, the tolyl may be 2-tolyl, 3-tolyl, or 4-tolyl, the xylenyl may be o-Xylene (ortho-xylene) or m-Xylene (meta-xylene), and the naphthyl may be 1-naphthyl or 2-naphthyl.

The $C_1$-$C_6$ alkyl may be a linear or branched alkyl such as methyl, ethyl, propyl, isopropyl, butyl, isobutyl, sec-butyl, or pentyl.

Preferably, $X_1$ may be OH or O—Y—Z, in which Y may be a carbonyl group, and Z may be a substituted phenyl group or naphthyl group. A substituent substituted in the phenyl group or naphthyl group may be preferably one or more amino groups, more preferably an amino group substituted in ortho or para position.

In the present invention, the $C_3$-$C_{12}$ saturated linear or branched alkyl means a chained hydrocarbon radical which does not have a double bond or a triple bond. For example, the $C_3$-$C_{12}$ saturated linear or branched alkyl comprises groups such as homologues or isomers comprising n-propyl, isopropyl, n-butyl, t-butyl, isobutyl, sec-butyl, pentyl, hexyl, heptyl, octyl, nonyl, decyl, undecyl, dodecyl, etc.

In the present invention, the $C_3$-$C_{12}$ unsaturated linear or branched alkyl refers to a linear chain or branched chain alkyl group having one or more double or triple bonds.

The $C_3$-$C_{12}$ alkyl as a linear chain or branched chain having one or more double or triple bonds is comprised in the category of the $C_3$-$C_{12}$ unsaturated linear or branched alkyl in the present invention. For example, although the $C_3$-$C_{12}$ alkyl may be pentenyl, hexenyl, heptenyl, octenyl, nonenyl, or the like having one or more double bonds, and may be hexadienyl, heptadienyl, octadienyl, or the like having two or more double bonds, the $C_3$-$C_{12}$ alkyl is not limited thereto, and the position of the double bonds may also be changed without a problem as long as the bond structure is maintained. Preferably, the $C_3$-$C_{12}$ alkyl may be heptadienyl having two double bonds.

In the present invention, the $C_3$-$C_{12}$ saturated or unsaturated linear or branched alkyl may be $C_5$-$C_{10}$ saturated or unsaturated linear or branched alkyl.

The $C_3$-$C_{12}$ alkenyl is a hydrocarbon having a double bond. Preferably, the $C_3$-$C_{12}$ alkenyl may be alkenyl which may have the maximum number of double bonds depending on the number of carbon atoms. For example, although the $C_3$-$C_{12}$ alkenyl may be pentadiene, hexatriene, heptatriene, octatetraene, etc., the $C_3$-$C_{12}$ alkenyl is not limited thereto, and may comprise all homologues or isomers capable of having maximum double bonds depending on the number of carbon atoms.

Specifically, the compound represented by Chemical Formula 1 according to the present invention may be any one selected from compounds represented by the following Chemical Formulas 2, and 4 to 6:

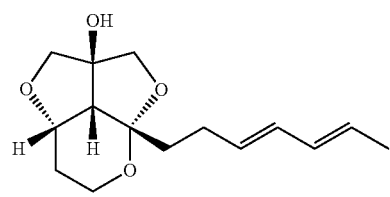

[Chemical Formula 2]

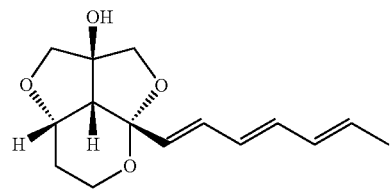

[Chemical Formula 4]

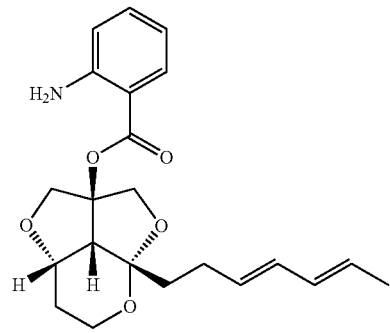

[Chemical Formula 5]

-continued

[Chemical Formula 6]

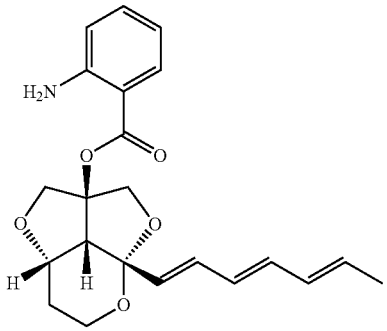

Specifically, the compound according to the present invention may be any one selected from the group consisting of the following compounds:

((3E,5E)-hepta-3,5-diene-1-yl)tetrahydro-2H, 6H,1,4,7-trioxacyclopenta[cd]indene-2a(3H)-ol;

((1E,3E,5E)-hepta-1,3,5-triene-1-yl)tetrahydro-2H,6H,1,4,7-trioxacyclopenta[cd]indene-2a(3H)-ol;

((3E,5E)-hepta-3,5-diene-1-yl)tetrahydro-2H,6H,1,4,7-trioxacyclopenta[cd]indene-2a(3H)-yl-2-aminobenzoate; and ((1E,3E,5E)-hepta-1,3,5-triene-1-yl)tetrahydro-2H,6H,1,4,7-trioxacyclopenta[cd]indene-2a(3H)-yl-2-aminobenzoate.

More specifically, the compound according to the present invention may be any one selected from the group consisting of the following compounds:

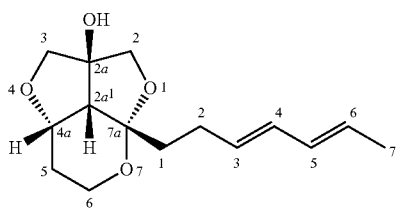

(2aS,2a¹R,4aS,7aS)-7a-((3E,5E)-hepta-3,5-diene-1-yl)tetrahydro-2H,6H,1,4,7-trioxacyclopenta[cd]indene-2a(3H)-ol;

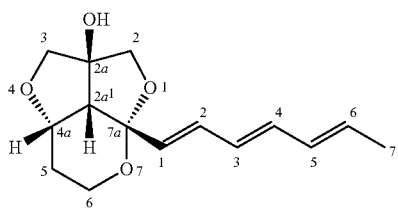

(2aS,2a¹R,4aS,7aS)-7a-((1E,3E,5E)-hepta-1,3,5-triene-1-yl)tetrahydro-2H, 6H,1,4,7-trioxacyclopenta[cd]indene-2a(3H)-ol;

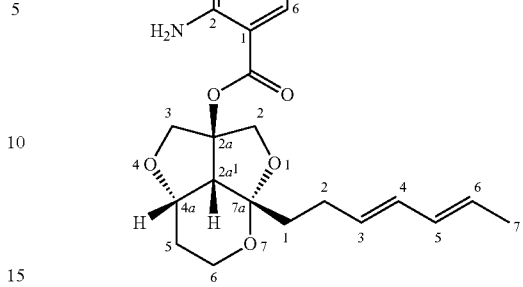

(2aS,2a¹R,4aS,7aS)-7a-((3E,5E)-hepta-3,5-diene-1-yl)tetrahydro-2H,6H,1,4,7-trioxacyclopenta[cd]indene-2a(3H)-yl-2-aminobenzoate; and

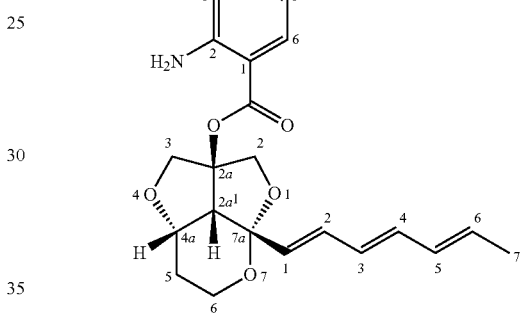

(2aS,2a¹R,4aS,7aS)-7a-((1E, 3E,5E)-hepta-1,3,5-triene-1-yl)tetrahydro-2H, 6H,1,4,7-trioxacyclopenta[cd]indene-2a(3H)-yl-2-aminobenzoate.

The compound represented by Chemical Formula 1 of the present invention may contain one or more asymmetric carbons, and may accordingly exist as racemate, a racemic mixture, a single enantiomer, a diastereomer mixture, or respective diastereomers.

These isomers can be separated by the conventional art. For example, the compound represented by Chemical Formula 1 can be separated by fractionation with column chromatography, high-performance liquid chromatography (HPLC), or the like. Alternatively, the respective stereoisomers of the compound represented by Chemical Formula 1 may be stereo-specifically synthesized using an optically pure starting material and/or reagent with known stereochemistry.

A term used in the present invention, "pharmaceutically acceptable salts" mean salts of the form which may be pharmaceutically used among salts, i.e., materials in which cations and anions are bonded by electrostatic attraction, and the pharmaceutically acceptable salts may generally comprise metal salts, salts with organic bases, salts with inorganic acids, salts with organic acids, salts with basic or acidic amino acids, etc. For example, the pharmaceutically acceptable salts may comprise: metal salts comprising alkali metal salts (sodium salts, potassium salts, and the like), alkali earth metal salts (calcium salts, magnesium salts, barium salts, and the like), aluminum salts, etc.; salts with organic bases comprising salts with triethylamine, pyridine, picoline, 2,6-lutidine, ethanolamine, diethanolamine, triethanolamine, cyclohexylamine, dicyclohexylamine, N,N-dibenzylethylenediamine, etc.; salts with inorganic acids comprising salts with hydrochloric acid, hydrobromic acid, nitric acid, sulfuric acid, phosphoric acid, etc.; salts with organic acids comprising salts with formic acid, acetic acid, trifluoroacetic acid, phthalic acid, fumaric acid, oxalic acid, tartaric acid, maleic acid, citric acid, succinic acid, methanesulfonic acid, benzenesulfonic acid, p-toluenesulfonic acid, etc.; salts with basic amino acids comprising salts with arginine, lysine, ornithine, etc.; and salts with acidic amino acids comprising salts with aspartic acid, glutamic acid, etc.

Preparation Method of Compound of Chemical Formula 1

The foregoing compound of Chemical Formula 1 may be secondary metabolites produced and isolated from a marine microbe *Streptomyces*.

Specifically, the present invention provides preparation methods of a compound represented by Chemical Formula 1 comprising:

a step (a) of culturing a strain of *Streptomyces* sp.;

a step (b) of performing an extraction process by adding a first organic solvent to the culture broth of *Streptomyces* strain;

a step (c) of obtaining a crude extract from the first organic solvent layer, and eluting the crude extract with water and a second organic solvent, thereby fractionating the crude extract; and a step (d) of isolating compounds from a fraction of the step (c).

In the step (a), the genus of *Streptomyces* may preferably be *Streptomyces miharaensis*. More specifically, the strain of *Streptomyces* sp. may be a *Streptomyces miharaensis* strain having 16S RNA (16S rRNA) gene sequencing (GenBank accession number KY569410).

The strain may be obtained by culturing in a liquid medium or a solid medium. The medium may comprise, for example, glucose, starch syrup, dextrin, starch, molasses, animal oil, or vegetable oil as a carbon source. The medium may comprise, for example, wheat bran, soybean meal, wheat, malt, cottonseed meal, fish scrap, corn steep liquor, beef stock, beef extract, tryptone, yeast extract, or the like as a nitrogen source. The medium may comprise table salt, potassium, magnesium, cobalt, chlorine, phosphoric acid, sulfuric acid, or inorganic salts promoting the generation of other ions as necessary.

Preferably, the medium may comprise glucose, yeast extract, tryptone, beef extract, glycerol, and sodium chloride. The culturing process may comprise performing shaking or static cultures under aerobic conditions. The culturing process may be performed at a culturing temperature, for example, of about 20 to 37° C., or about 25 to 30° C.

The step (b) of performing the extraction process by adding the first organic solvent to the culture of *Streptomyces* strain may further comprise the step of separating the cells before adding the first organic solvent. After separating the cells, a supernatant may be extracted with ethyl acetate and/or alcohols having 1 to 4 carbon atoms, etc.

This extract of the step (b) may be provided as a crude extract through a conventional drying process or the like.

The step (c) comprises fractionating the crude extract by eluting the crude extract with water and the second organic solvent. This separation is a step of fractionating the eluted crude extract after gradient elution of the crude extract with a sequential concentration of water and the second organic solvent. Here, the second organic solvent is preferably alcohols having 1 to 4 carbon atoms comprising methanol, ethanol, propanol, etc.

The process of separating the compound of Chemical Formula 1 from the fraction in the step (d) may be performed using, for example, a chromatography. For example, the chromatography may be a column chromatography, a planar chromatography, a paper chromatography, or a thin film chromatography depending on the form of a stationary phase. Alternatively, the chromatography may be a gas chromatography, a liquid chromatography, or an affinity chromatography depending on physical properties of a mobile phase. The liquid chromatography may be, for example, a high-performance liquid chromatography (HPLC). The chromatography may be, for example, an ion exchange chromatography or a size exclusion chromatography depending on separation methods. The chromatography may be, for example, a normal phase chromatography or a reverse phase chromatography.

Compounds 1 to 4 which is represented by Chemical Formulas 2, 4, 5 or 6 may be separated through the aforementioned processes.

Further, the present invention provides a compound represented by the following Chemical Formula 3 by carrying out reduction and methylation reactions of the compound of Chemical Formula 2.

[Chemial Formula 3]

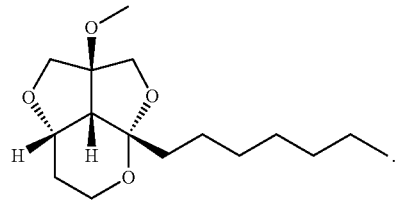

Use of Compound of Chemical Formula 1

The present invention provides a pharmaceutical composition comprising the compound represented by the above-mentioned Chemical Formula 1, the optical isomer or the pharmaceutically acceptable salt thereof.

Furthermore, the present invention provides a pharmaceutical composition comprising the compound represented by the above-mentioned Chemical Formula 1, the optical isomer or the pharmaceutically acceptable salt thereof; and pharmaceutically acceptable excipients.

The present invention relates to a pharmaceutical composition for the prevention or treatment of neurodegenerative diseases comprising the compound of the above-mentioned Chemical Formula 1, the optical isomer or the pharmaceutically acceptable salt thereof as effective components. Here, although the neurodegenerative diseases may be one or more selected from the group consisting of Alzheimer's disease, Lou Gehrig's disease, Parkinson's disease, Huntington's disease, MELAS syndrome, and multiple sclerosis, the neurodegenerative diseases are not limited thereto.

The above-mentioned neurodegenerative diseases may be generated by inflammatory neurodegeneration, etc. The composition according to the present invention exhibits excellent effects in the treatment of the diseases by controlling inflammatory factors involved in diseases with respect to inflammation generated in microglial cells, etc., and significantly reducing the generation of NO.

A pharmaceutical composition according to the present invention may further comprise one or more pharmaceutically acceptable excipients for the purpose of administration in addition to the compound of the above-mentioned Chemical Formula 1, the optical isomer or the pharmaceutically acceptable salt thereof. For example, a pharmaceutically acceptable carrier may comprise saline solution, sterilized water, Ringer solution, buffered saline, dextrose solution, maltodextrin solution, glycerol, ethanol, and mixtures of one or more thereof, and other conventional excipients comprising an antioxidant, a buffer solution, a bacteriostatic agent, and the like may be added as necessary. Furthermore, the pharmaceutical composition according to the present invention may be formulated into injectable formulations such as an aqueous solution, a suspension, an emulsion, etc., and pills, capsules, granules, or tablets by additionally adding a diluent, a dispersant, a surfactant, a binding agent, and a lubricating agent. Accordingly, the pharmaceutical composition according to the present invention may be patches, liquid medicines, pills, capsules, granules, tablets, suppositories, etc. These formulations may be manufactured by ordinary methods used in the formulation in the related art, or methods disclosed in Remington's Pharmaceutical Science (recent edition), Mack Publishing Company, Easton Pa., and may be formulated into various formulations depending on respective diseases or components.

The pharmaceutical composition according to the present invention may be administered orally or administered parenterally (for example, for intravenous, subcutaneous, intraperitoneal or local application) depending on purposed methods, and the dosage range varies depending on weight, age, gender, health condition, diet, administration time, administration method, excretion rate, disease severity, and so on of a patient. A compound of Chemical Formula 1 according to the present invention may have a daily dosage of about 0.01 to 1,000 mg/kg, preferably 0.1 to 100 mg/kg, and may be administered once or several times a day.

The pharmaceutical composition according to the present invention may further comprise one or more effective components showing equal or similar medicinal effects in addition to derivative compounds of the above-mentioned Chemical Formula 1, the optical isomer or the pharmaceutically acceptable salt thereof.

The present invention provides methods of treating neurodegenerative diseases, comprising administering therapeutically effective amounts of the compound of the above-mentioned Chemical Formula 1, the optical isomer or the pharmaceutically acceptable salt thereof to an object.

The term "therapeutically effective amount" used in the present invention refers to the amount of the compound of the above-mentioned Chemical Formula 1 which is effective in the treatment of neurodegenerative diseases.

A treatment method according to the present invention not only manages the disease before it develops, but also relieves or suppresses the symptoms of the disease by administering the compound of the above-mentioned Chemical Formula 1. In the management of the diseases, the preventive or therapeutic dosage of a specific active component may vary depending on nature and severity of diseases or conditions, and path to which the active component is administered. The dosage and the frequency of the dosage may vary depending on the age, weight, and response of individual patients. Appropriate dosage and usage may be easily selected by those skilled in the art who take these factors into account. Furthermore, a treatment method according to the present invention may further comprise administering a therapeutically effective amount of an additional active agent which is helpful for the treatment of the diseases along with the compound of the above-mentioned Chemical Formula 1, and the additional active agent along with the compound of the above-mentioned Chemical Formula 1 may exhibit synergistic or auxiliary effects.

The present invention provides a food composition for the prevention or improvement of neurodegenerative diseases, comprising the compound of the above-mentioned Chemical Formula 1, the optical isomer or the pharmaceutically acceptable salt thereof as effective components.

A food composition according to the present invention may be used as a health functional food. The "health functional food" means a food manufactured and processed using raw materials or ingredients having the functionality useful in the human body in accordance with Functional Foods for Health Act No. 6727, and the "functionality" means ingesting the food for the purpose of controlling nutrients with respect to structure and function of the human body, or obtaining effects useful in health uses comprising physiological action, etc.

A food composition according to the present invention may comprise ordinary food additives, and whether the "food additives" are suitable or not may be determined by specifications and criteria for items concerned in accordance with the General Rules and General Test Methods, etc. of Korean Food Additives Codex approved by the Korea Food and Drug Administration unless otherwise provided.

For the purpose of preventing and/or improving neurodegenerative diseases, a food composition according to the present invention may comprise 0.01 to 95 wt %, preferably 1 to 80 wt % of the compound of the above-mentioned Chemical Formula 1 with respect to the total weight of the composition. Furthermore, for the purpose of preventing and/or improving neurodegenerative diseases, a food composition according to the present invention may be prepared and processed into the form of tablets, capsules, powders, granules, liquids, pills, beverages, and the like.

Furthermore, the present invention provides a pharmaceutical composition comprising the compound of Chemical Formula 1 which is used in the treatment of neurodegenerative diseases, the optical isomer or the pharmaceutically acceptable salt thereof.

Furthermore, the present invention provides a use of the compound of Chemical Formula 1, the optical isomer or the pharmaceutically acceptable salt thereof for manufacturing medicaments for the treatment of the neurodegenerative diseases. The compound of the above-mentioned Chemical Formula 1 for manufacturing medicaments may comprise mixtures of an adjuvant, a diluent, a carrier, and the like which are accepted, and the compound of the above-mentioned Chemical Formula 1 together with other active agents are prepared into a composite formulation so that the compound of the above-mentioned Chemical Formula 1 may have synergistic action of the active agents.

Details mentioned in compositions, uses, and treatment methods according to the present invention are equally applied as long as the details do not contradict each other.

EXAMPLES

Hereinafter, the present invention will be described in more detail through Examples. However, the following Examples are provided only to understand the present invention more easily, and the scope of the present invention is not limited thereto.

Experimental Equipment 1D ($^1$H and $^{13}$C), 2D (COSY, ROESY, HSQC, HMBC) NMR spectra were obtained using a Varian Unity 500 MHz spectroscope. UV spectra were obtained using a Shimadzu UV-1650PC spectrophotometer. IR spectra were obtained using a JASCO FT/IR-4100 spectrophotometer. Optical rotations were measured using a Rudolph Research Analytical (Autopol III) polarimeter. High resolution electrospray ionization mass spectroscopy (HRESIMS) spectra were recorded using a Shimadzu LC/MS-IT-TOF mass spectrometer. High-Performance Liquid Chromatography (HPLC) was performed using an RI-101 (Shodex) detector and a PrimeLine Binary pump. Semi-preparative HPLC was performed using an ODS column (YMC-Pack-ODS-A, 250×10 mm, i.d, 5 μm) and a silica column (YMC-Pack-SIL, 250× 10 mm, i.d, 5 μm). Analytical HPLC was performed using an ODS column (YMC-Pack-ODS-A, 250×4.6 mm, i.d, 5 μm).

Mass Culturing of *Streptomyces* Stain

A 151KO-143 strain was isolated from a mangrove tree collected in Kosrae Island. As results of 16S rRNA gene sequencing (GenBank accession number KY569410), the strain was identified to be *Streptomyces miharaensis* of *Streptomyces* sp.

The isolated 151KO-143 strain was grown on a Bennett (BN) agar plate at 28° C. for 7 days, and then inoculated into a flask containing 50 mL of BN liquid medium (containing 10 g of glucose, 1 g of yeast extract, 2 g of tryptone, 1 g of beef extract, 5 g of glycerol, and 32 g of NaCl in 1 L of distilled water). After cultivation at 130 rpm and 28° C. for 7 days, 10 mL of a culture solution in a 50 ML flask was used to inoculate 1 L of BN medium into a 2 L flask under the same conditions for 7 days. 1 L of the culture in 2 L flask (×10) and a 100 L fermenter were used for 10 L and 60 L large-scale cultivation. 10 L and 60 L cultivations were cultured at 28° C. for 7 days and 4 days, respectively.

Example 1. Extraction and Separation of Compounds

The culture broth (total 70 L) was separated into the cells and the supernatant by centrifugation and then extracted with EtOAc. The EtOAc extract was evaporated to obtain crude extract (5 g). The crude extract was fractionated by flash column chromatography on ODS using a stepwise elution with a combination of MeOH/H$_2$O (1:4, 2:3, 3:2, 4:1, and 100% MeOH).

The fraction eluted with MeOH/H$_2$O (3:2) was isocratic eluted with 52% MeOH in H$_2$O and purified by semi-preparative reverse-phase HPLC (YMCPack-ODS-A, 250× 10 mm i.d, 5 μm, flow rate 3.5 mL/min, RI detector) to obtain compound 1 (10.4 mg, $t_R$=36 min) and compound 2 (2.9 mg, $t_R$=24 min) in the form of a viscous yellow oil.

The fraction eluted with MeOH/H$_2$O (4:1) was isocratic eluted with ACN-MeOH—H$_2$O (3:3:4) and purified by an analytical reversed-phase HPLC (YMC-Pack-ODS-A, 250× 4.6 mm i.d, 5 μm, flow rate 2.0 mL/min, RI detector) to obtain compound 3 (2.5 mg, $t_R$=18.5 min) and compound 4 (1.0 mg, $t_R$=12.5 min) in the form of a purple amorphous solid.

Example 2. Structure Determination of Compounds

The analysis results of the optical purity; IR; UV; HRESIMS of compounds 1 to 4 are summarized as follows.

Compound 1: $[\alpha]_D^{25}$ −23.3 (c 0.1, MeOH); IR $\nu_{max}$ 3606, 2958, 2922, 2869, 1358, 1267, 1163, 1053, 990 cm$^{-1}$; UV (MeOH) $\lambda_{max}$ (log ε) 236 (2.57) nm; HRESIMS m/z 289.1412 [M+Na]$^+$ (calcd for 289.1416, C$_{15}$H$_{22}$O$_4$Na).

Compound 2: $[\alpha]_D^{25}$ −30.0 (c 0.1, MeOH); IR $\nu_{max}$ 3390, 2914, 1649, 1252, 678 cm$^{-1}$; UV (MeOH) $\lambda_{max}$ (log ε) 246 (2.59) nm; HRESIMS m/z 287.1262 [M+Na](calcd for 287.1259, C$_{15}$H$_{20}$O$_4$Na).

Compound 3: $[\alpha]_D^{25}$ −16.6 (c 0.1, MeOH); IR $\nu_{max}$ 3702, 2975, 2861, 2355, 1671, 1341, 1064, 1007 cm$^{-1}$; UV (MeOH) $\lambda_{max}$ (log ε) 240 (3.57), 342 (3.39), 406 (3.24) nm; HRESIMS m/z 384.1813 [M-H]$^-$ (calcd for 384.1811, C$_{22}$H$_{27}$NO$_5$).

Compound 4: $[\alpha]_D^{25}$ −30.0 (c 0.1, MeOH); IR $\nu_{max}$ 3698, 2954, 2851, 2366, 1348, 1057, 1011 cm$^{-1}$; UV (MeOH) $\lambda_{max}$ 240 (3.54), 334 (2.99) nm; HRESIMS m/z 382.1656 [M-H]$^-$ (calcd for 382.1654, C$_{22}$H$_{25}$NO$_5$).

Example 2-1. Structure Determination of Compound 1

The structure of compound 1 is as shown in Chemical Formula 2 below, and the structure was determined as follows.

[Chemical Formula 2]

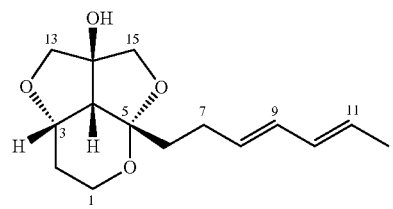

(Numbers on the above chemical structure comprising 1, 3, 5, 7, 9, 11, 13, and 15 are arbitrary numbers attached for reference of the following structural analysis)

Structural Determination by Analysis of HRESIMS, NMR, and HMBC Data

Figure 2:
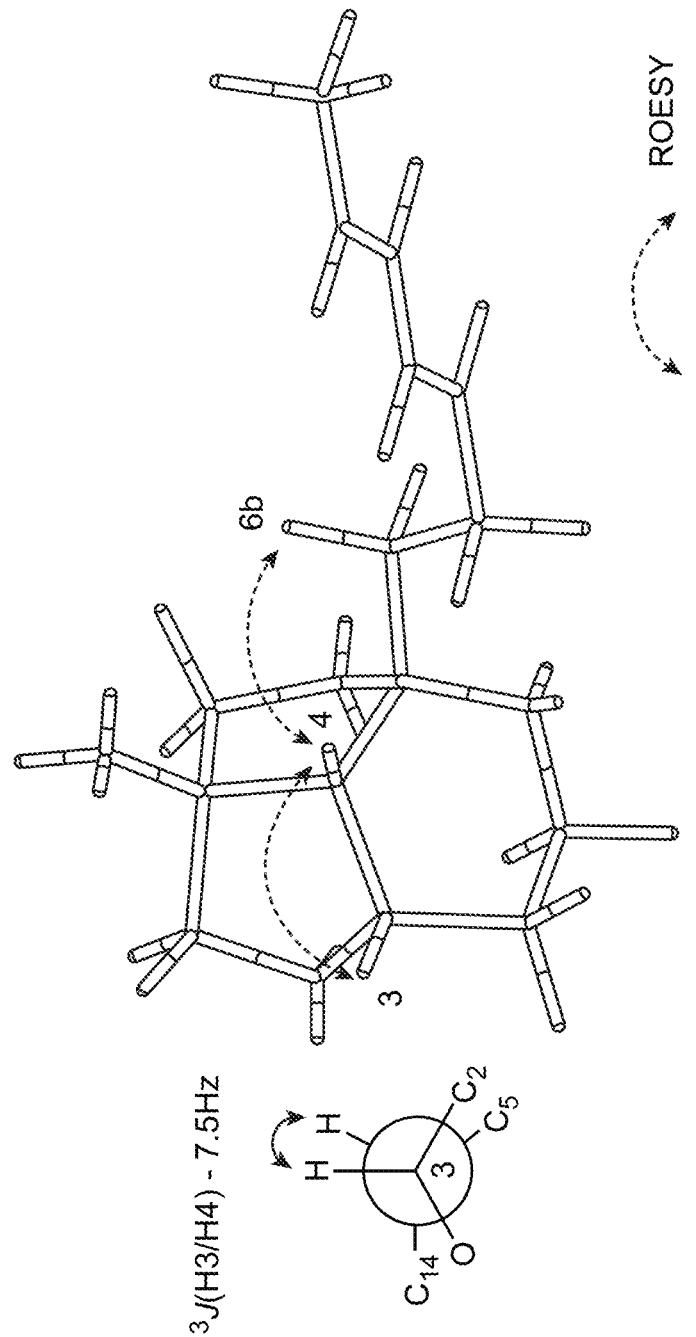
FIG. 2 illustrates the structure and stereochemistry of compound 1 based on a coupling constant $^3J_{(H3/H4)}$ and ROESY correlations.

Chemical Formula of compound 1 was determined as C$_{15}$H$_{22}$O$_4$ by HRESIMS analysis (m/z 289.1412 [M+Na]$^+$, 289.1416 as a calculated value). $^1$H NMR spectra of compound 1 showed the presence of a methyl group at $\delta_H$ 1.70, four olefinic protons at $\delta_H$ 5.54×2 and $\delta_H$ 6.00×2, and six characteristic protons at $\delta_H$ 4.02, 3.98, 3.91, 3.80, 3.63, and 3.51 for three oxygenated methylenes. The $^{13}$C NMR data and HSQC spectra of compound 1 indicated the presence of three oxygenated methylenes, three methylenes, six methines, one methyl, and two quaternary carbons. Detailed analyses of the 2D NMR ($^1$H-$^1$H COSY, HSQC, and HMBC) data for compound 1 led to the assignment of the spin systems and their correlations. The $^1$H-$^1$H COSY correlations of H$_2$-1/H$_2$-2/H-3/H-4 and HMBC correlations from H$_2$-1 and H-3 to the quaternary carbon C-5 suggested the presence of a six-membered ring system (A ring in FIG. 1a) connected to three oxygen atoms. The presence of an unsaturated carbon chain was revealed by a proton spin system of H$_2$-6/H$_2$-7/H-8/H-9/H-10/H-11/H$_3$-12. In the HMBC spectrum, the correlations from H$_2$-6 to C-5 and H-4 to C-6 suggested that the side chain is connected to the A ring. The HMBC correlations from H$_2$-13 to C-14 and C-15 and from H$_2$-15 to C-13 and C-14 suggested that compound 1 possesses a glycerol moiety. Afterward, the linkage of the partial structures was deduced from the key HMBC correlations from H-4 to C-13 and C-14 and from H$_2$-15 to C-4 and C-5 (FIG. 2.). By detailed analysis of the 2D NMR data combined with the five degrees of unsaturation, the planar structure of compound 1 was elucidated to possess a rare 6/5/5 tricyclic ring system. The $^3J_{H,H}$ coupling constants for H-8/H-9 (14.0 Hz) and H-10/H-11 (14.0 Hz) were consistent with an E,E geometry of the conjugated diene in the side chain. Finally, the unique ring system of compound 1 was found to have a rigid conformation on the basis of general stereochemical considerations.

Reduction and Methylation of Compound 1

To avoid unnecessary byproduct formation, compound 1 was hydrogenated prior to methylation. Compound 1 (7.0 mg) in ethanol (200 μL) was added Pd/C (0.35 mg) under hydrogen gas for 2 hr. The reaction mixture was evaporated under reduced pressure and was purified by a flash open column of silica gel to remove Pd/C. The hydrogenated compound 1 in DMF (0.2 mL) was added NaH (3 mg) and MeI (5 μL). The mixture was stirred at 0° C. for 2 hours. After checking the new spot with TLC, the reaction mixture was treated with enough LiCl to remove DMF and extracted with EtOAc. The combined EtOAc extracts were evaporated under reduced pressure. The resulting residue was purified by a flash open column of silica gel to give hydrogenated and methylated compound 1 as a yellow viscous oil.

[Chemial Formula 3]

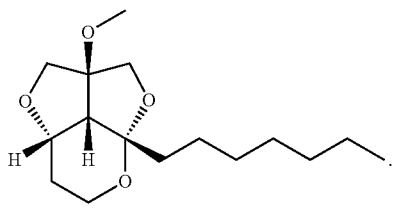

Absolute Configuration Analysis of Compound 1

Figure 3:
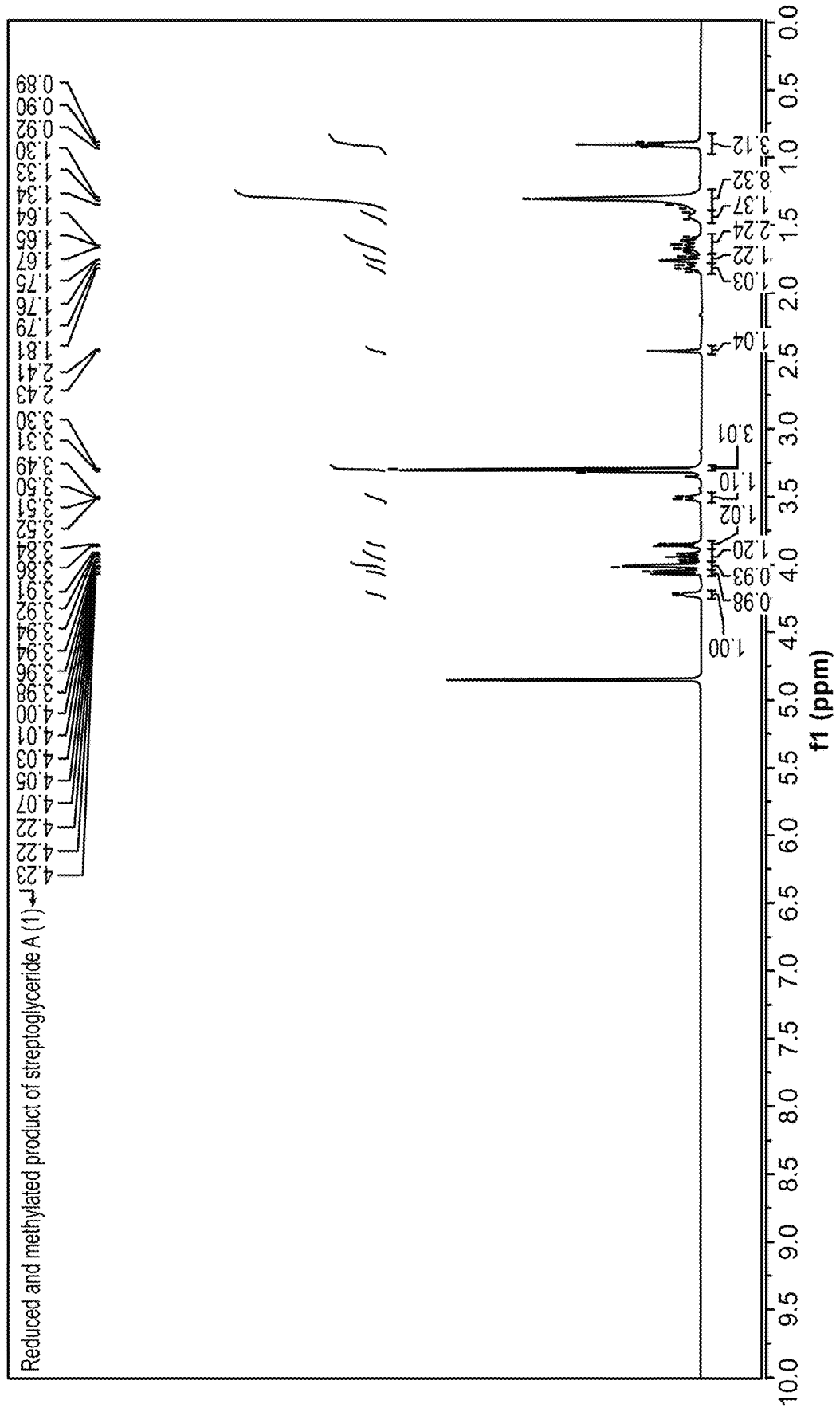
FIG. 3 illustrates a $^1$H NMR spectrum for the reduced and methylated derivative of compound 1.
Figure 4:
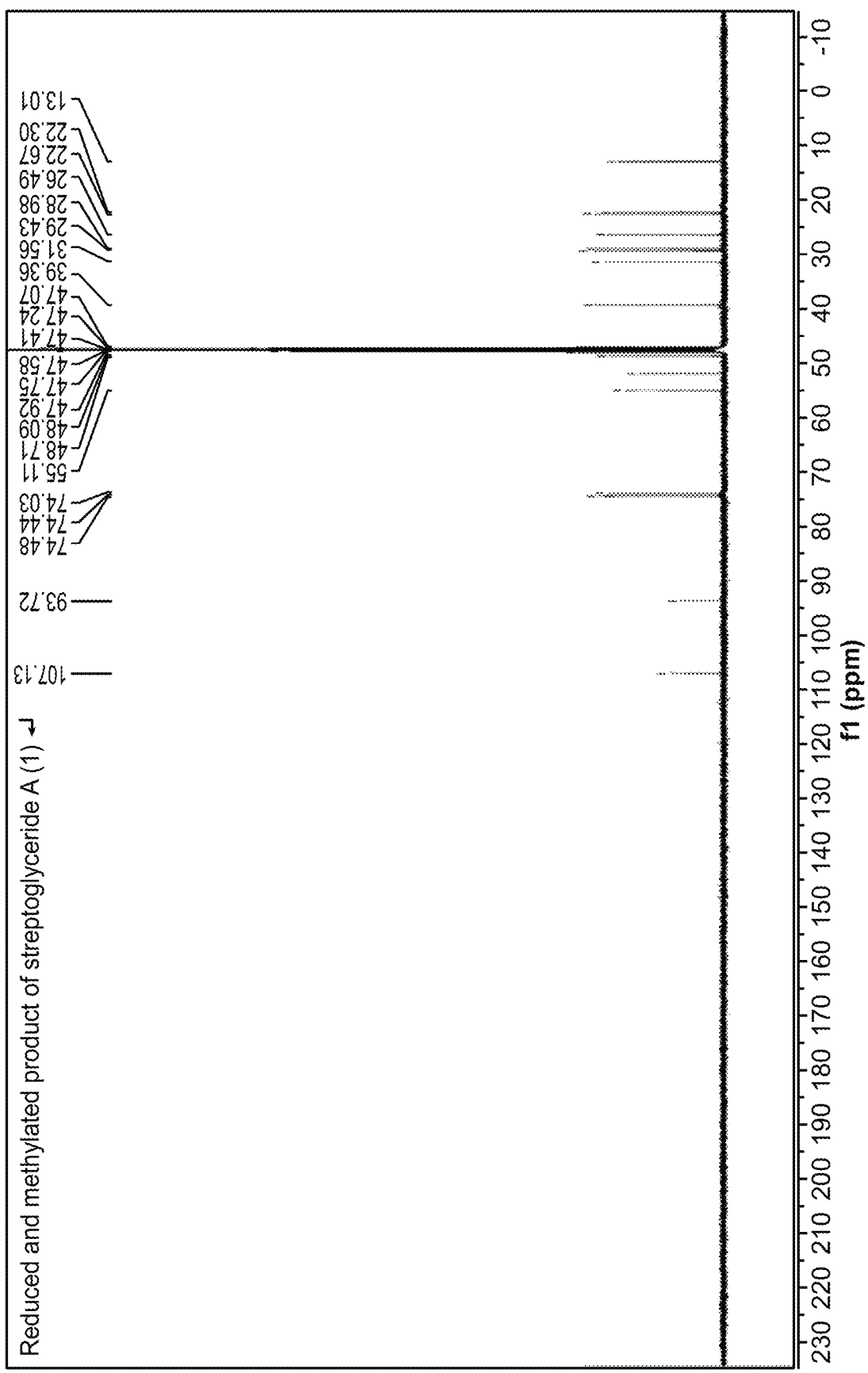
FIG. 4 illustrates a $^{13}$C NMR spectrum for the reduced and methylated derivative of compound 1.
Figure 5:
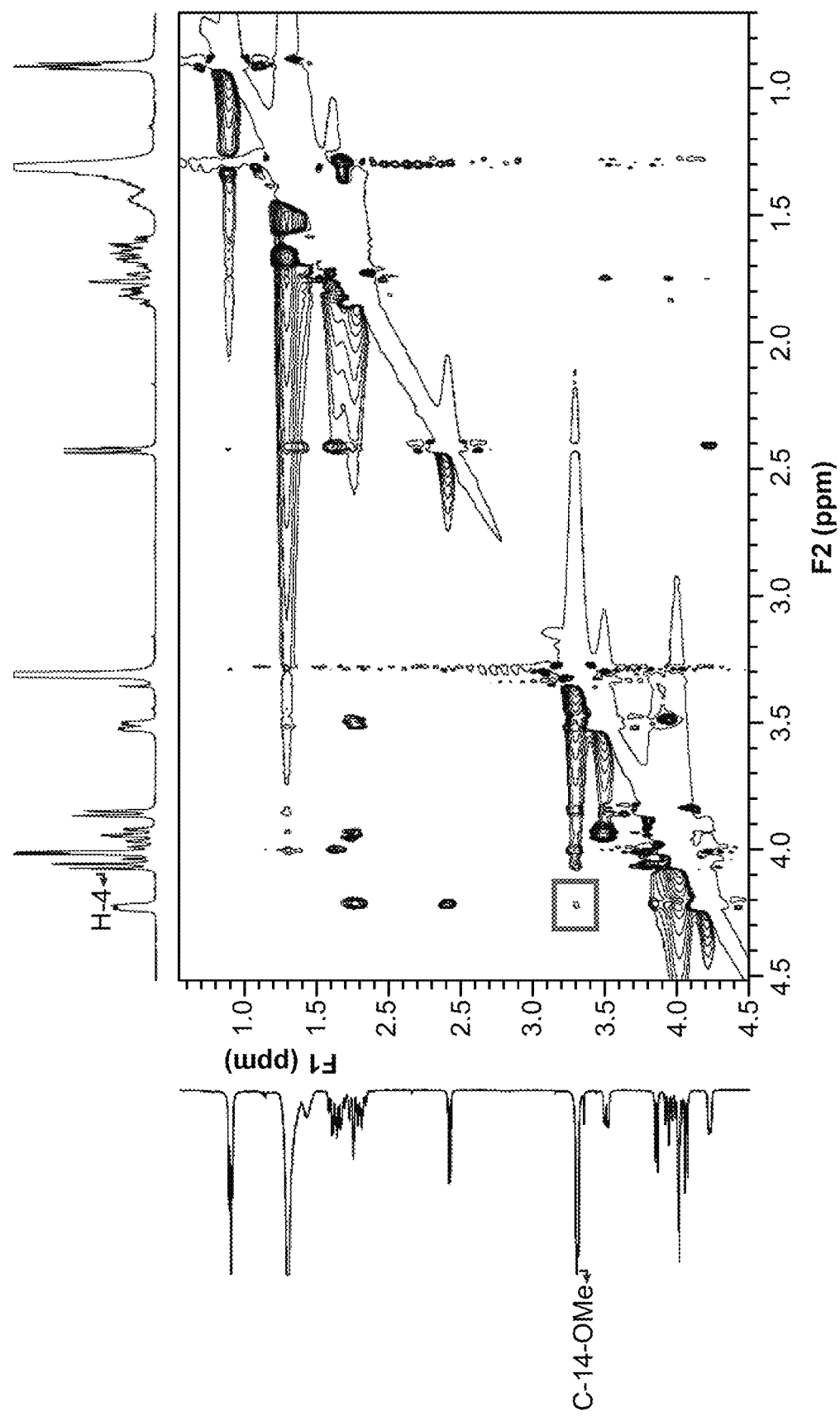
FIG. 5 illustrates a ROESY spectrum for the reduced and methylated derivative of compound 1.

First, the relative structure of compound 1 was determined by analyzing proton-proton coupling constant and ROESY correlation of compound 1 and a methylation derivative (Chemical Formula 3) of compound 1. The ROESY correlation between H-3 and H-4 indicated that these protons were disposed on the same face. Coupling constants (7.5 Hz) of H-3 and H-4 indicated that these two protons were located in a syn-arrangement (FIG. 2). Additionally, a strong ROESY correlation between H-4 and H-6b indicated that carbon chains of H-4 and compound 1 were on the same face. Methylation of compound 1 was conducted to determine the orientation of C-14-OH. The key ROESY correlation from 14-OMe of the methylated derivative of compound 1 to H-4 revealed that C-14-OMe and H-4 are cofacial (FIGS. 3 to 5). Thus, there were only two possible structures for compound 1, with absolute configurations of 1A (3S,4R,5S,14S) and 1B (3R,4S,5R,14R) (based on carbon numbers according to reference numbering of the above-mentioned numbers 1, 3, 5, 7, 9, 11, 13, and 15).

Figure 6:
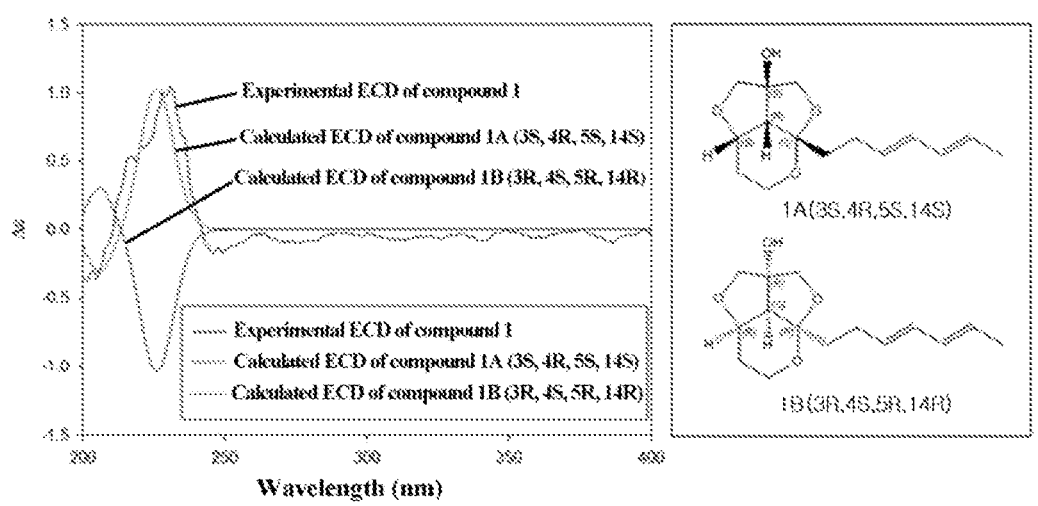
FIG. 6 illustrates an experimental ECD spectrum of compound 1, a calculated ECD spectrum of a possible enantiomer compound 1A (3S, 4R, 5S, and 14S) of compound 1, and a calculated ECD spectrum of an enantiomer compound 1B (3R, 4S, 5R, and 14R) of compound 1 (left), and shows the structures of compounds 1A and 1B.

In order to determine the absolute structure of compound 1, an experimental ECD curve of the compound 1 and calculated ECD curves of compounds 1A and 1B were compared (FIG. 4). A structure of minimizing energies of two enantiomers of compound 1 was calculated at a level from B3LYP/def2-TZVPP//B3LYP/def-SV(P) to TD-DFT with respect to all atoms using Turbomole 6.5. The experimental ECD curve of compound 1 showed a positive Cotton effect at 230 nm, which is consistent with the calculated ECD curve of compound 1A, whereas the other enantiomer, compound 1B, indicated the opposite ECD curve (FIG. 6.).

Therefore, the absolute configuration of the stereogenic centers of the compound 1 was determined to be the same as compound 1A (3S, 4R, 5S, and 14S).

Example 2-2. Structure Determination of Compound 2

The structure of compound 2 is as shown in Chemical Formula 4 below, and the structure was determined as follows.

[Chemial Formula 4]

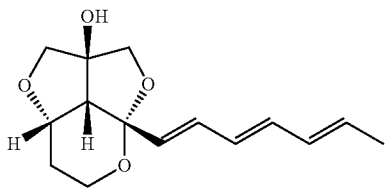

As a result of HRESIMS analysis (m/z 287.1262 [M+Na]$^+$, 287.1259 calculated value), the chemical formula of compound 2 was determined to be $C_{15}H_{20}O_4$ which was 2 mass units lower than compound 1. The $^1$H NMR data for compound 2 were similar to those of compound 1, differing only by the presence of two additional olefin signals and the absence of two methylenes. Signals for C-6 and C-7 saturated carbons were replaced with two unsaturated carbons of $\delta_C$ 130.1 and 132.4 respectively. The presence of one more double bond in the side chain than in compound 1 was confirmed by the $^1$H-$^1$H COSY and HMBC correlations. Nearly the same chemical shifts and 2D NMR correlations supported that compound 2 had the same planar structure as compound 1 except for the presence of an additional double bond, as indicated by the molecular formula. Furthermore, the E,E,E geometry of the conjugated triene in the side chain was determined by the $^3J_{H,H}$ values (14.5-15.5 Hz).

Example 2-3. Structure Determination of Compound 3

The structure of compound 3 is as shown in Chemical Formula 5 below, and the structure was determined as follows.

[Chemical Formula 5]

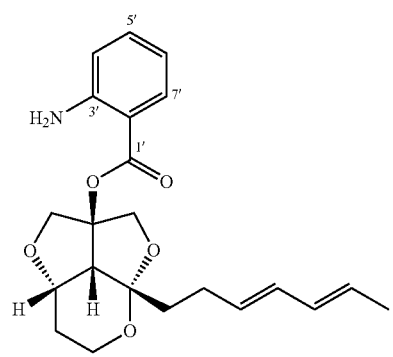

(Attached Numbers on the above chemical structure comprising 1', 3', 5', and 7' are arbitrary numbers for reference, and preceding numbers 1, 3, 5, 7, 9, 11, 13, and 15 are also attached for reference in the following structural analysis)

Figure 7:
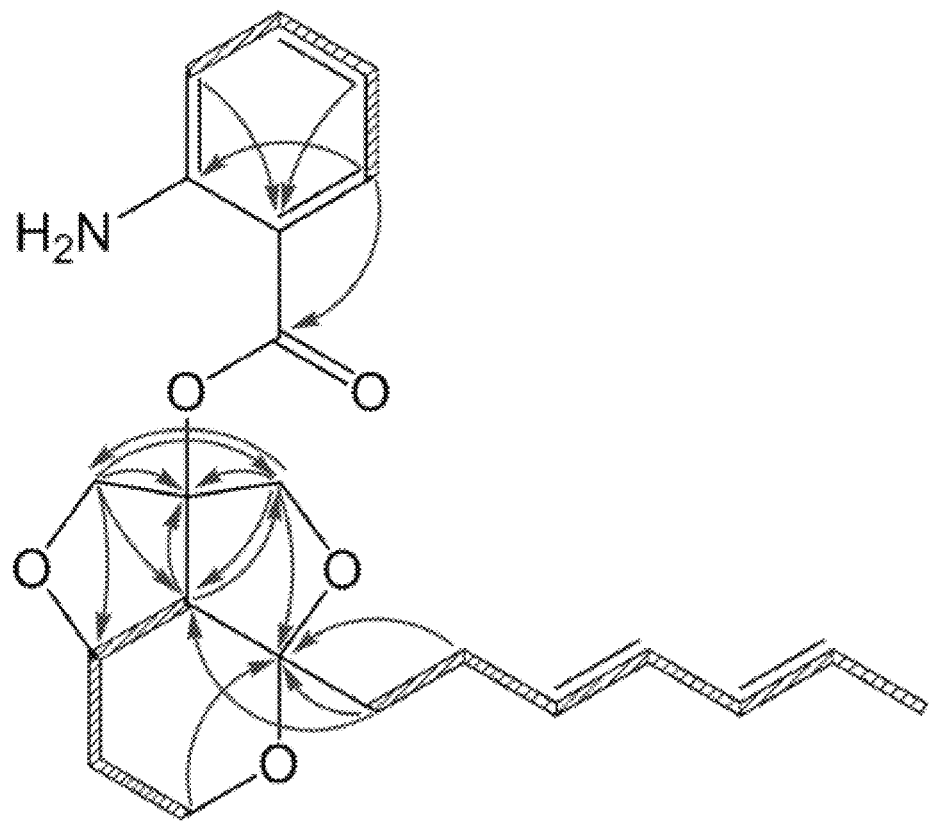
FIG. 7 illustrates key COSY (dashed line) and HMBC correlations (solid line) of compound 3.
Figure 7:
Figure 7:
Figure 8:
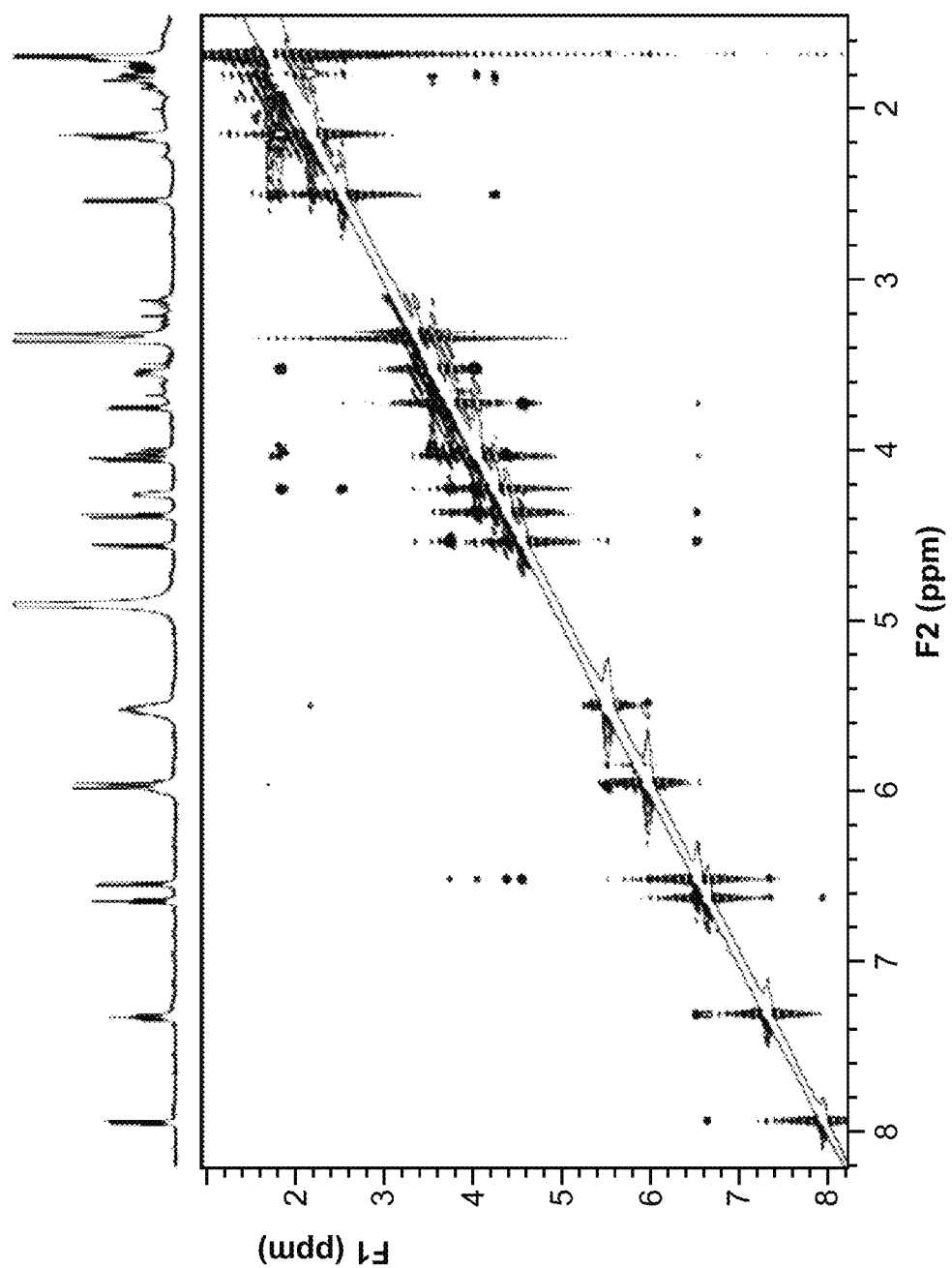
FIG. 8 illustrates a ROESY spectrum of compound 3.

As a result of HRESIMS analysis (m/z 384.1813 [M-H]⁻, 384.1811 calculated value), the chemical formula of compound 3 was determined to be $C_{22}H_{27}NO_5$. $^1$H NMR data of compound 3 were similar to those of compound 1 except for $H_2$-13 ($\delta_H$ 3.75, 4.56) and $H_2$-15 ($\delta_H$ 4.05, 4.38) which had been significantly downfield shifted. $^1$H and $^{13}$C NMR data of compound 3 showed additional signals for four aromatic protons at $\delta_H$ 6.54, 6.64, 7.32, and 7.94, and three quaternary carbons at $\delta_C$ 111.4, 149.2, and 170.7. Additionally, the presence of the 2-aminobenzoate moiety was confirmed by observing a proton spin system of H-4'/H-5'/H-6'/H-7', an HMBC correlation between H-7', and C-1' and C-3', and an HMBC correlation between H-4', and H-6' and C-2' (FIG. 7). Finally, the planar structure of compound 3 was determined by attachment of the 2-aminobenzoate to 14-OH of compound 1, as confirmed by the ROESY correlations between H-4' and $H_2$-13 as well as $H_2$-15 (FIG. 8) and supported by the downfield-shifted signals of $H_2$-13 and $H_2$-15 compared with those of compound 1.

Example 2-4. Structure Determination of Compound 4

The structure of compound 4 is as shown in Chemical Formula 6 below, and the structure was determined as follows.

[Chemical Formula 6]

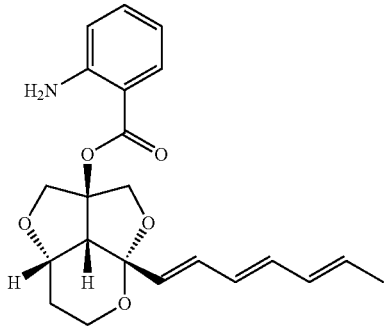

(Preceding numbers 1', 3', 5', 7, 1, 3, 5, 7, 9, 11, 13, and 15 are also entered for reference in the following structural analysis)

As a result of HRESIMS analysis (m/z 382.1656 [M-H]⁻, 382.1654 calculated value), the chemical formula of compound 4 was determined to be $C_{22}H_{25}NO_5$ which was 2 mass units lower than compound 3. The $^1$H NMR data for compound 4 were similar to those of compound 3, differing only by the presence of two additional olefin signals, as in compound 2. Signals for the C-6 ($\delta_C$ 39.3) and C-7 ($\delta_C$ 25.9) saturated carbons in compound 3 were replaced by two unsaturated carbons at $\delta_C$ 130.1 and 132.4, respectively. The presence of three disubstituted olefins in the side chain was confirmed by the $^1$H-$^1$H COSY and HMBC correlations. Almost the same chemical shifts and 2D NMR correlations in compound 4 compared with compound 3 suggested that compound 4 has the same backbone as compound 3 with an additional double bond.

Comparison of the optical rotation values and chemical shifts of compounds 1-4 suggested that they have the same backbone and absolute configuration of 3S,4R,5S,14S.

$^1$H NMR (CD$_3$OD, 500 MHz) and $^{13}$C NMR (CD$_3$OD, 125 MHz) data of compounds 1-4 are as shown in Tables 1 and 2 below.

TABLE 1

| | Compound 1 | | Compound 2 | |
|---|---|---|---|---|
| No. | $\delta_H$ (J, Hz) | $\delta_C$ | $\delta_H$ (J, Hz) | $\delta_C$ |
| 1a | 3.51, dd (11.0,4.0) | 55.0 | 3.55, dd (11.0, 3.5) | 55.2 |
| 1b | 3.91, dd (11.0, 2.0) | | 4.01, overlapped | |
| 2 | 1.74, 1.82, m | 26.5 | 1.85, m | 26.2 |
| 3 | 4.26, t like (4.0) | 74.5 | 4.29, t (3.5) | 74.5 |
| 4 | 2.24, d (7.5) | 51.4 | 2.39, d (7.5) | 51.6 |
| 5 | | 106.9 | | 104.9 |
| 6a | 1.74, m | 39.2 | 5.68, d (15.5) | 132.4 |
| 6b | 1.80, m | | | |
| 7 | 2.16, m | 25.9 | 6.41, dd (15.5, 10.5) | 130.1 |
| 8 | 5.54, m | 130.8 | 6.12, dd (14.5, 11.0) | 108.8 |
| 9 | 6.00, dd (14.0, 10.0) | 130.3 | 6.27, dd (14.5, 10.5) | 134.6 |
| 10 | 6.00, dd (14.0, 10.0) | 131.6 | 6.12, dd (14.5, 10.5) | 130.3 |
| 11 | 5.55, m | 126.0 | 5.76, m | 131.4 |
| 12 | 1.70, d (6.0) | 16.7 | 1.77, d (7.0) | 16.9 |
| 13a | 3.80, d (9.5) | 77.2 | 3.80, dd (9.0, 1.5) | 77.8 |
| 13b | 3.63, d (9.5) | | 3.66 dd (9.5, 1.5) | |
| 14 | | 87.5 | | 87.2 |
| 15a | 4.02, d (9.5) | 77.3 | 4.01, overlapped | 77.1 |
| 15b | 3.98, d (9.5) | | 4.01, overlapped | |

TABLE 2

| | Compound 3 | | Compound 4 | |
|---|---|---|---|---|
| No. | $\delta_H$ (J, Hz) | $\delta_C$ | $\delta_H$ (J, Hz) | $\delta_C$ |
| 1a | 3.54, dd (11.5, 2.5) | 55.1 | 3.59, dd (11.0, 3.0) | 55.2 |
| 1b | 4.00, dd (12.5, 2.5) | | 4.10, t (10.0) | |
| 2 | 1.83, m | 26.2 | 1.87, m | 25.9 |
| 3 | 4.25, t (4.0) | 73.6 | 4.32, t like (4.0) | 73.7 |
| 4 | 2.53, d (7.5) | 53.0 | 2.71, d (7.5) | 52.9 |
| 5 | | 106.5 | | 104.7 |
| 6a | 1.72, m | 39.3 | 5.65, d (15.5) | 131.8 |
| 6b | 1.80, m | | | |
| 7 | 2.16, dt (9.5, 7.5) | 25.9 | 6.38, dd (15.5, 10.5) | 130.1 |
| 8 | 5.51, m | 130.8 | 6.07, dd (14.5, 11.0) | 130.6 |
| 9 | 5.96, dd (14.0, 10.0) | 130.4 | 6.22, dd (14.5, 10.5) | 134.8 |
| 10 | 5.96, dd (14.0, 10.0) | 131.6 | 6.07, dd (14.5, 10.5) | 128.6 |
| 11 | 5.51, m | 126.1 | 5.73, m | 131.4 |
| 12 | 1.68, d (6.5) | 16.7 | 1.74, d (6.5) | 16.9 |
| 13a | 4.56, d (9.0) | 77.7 | 4.59, d (9.0) | 78.2 |
| 13b | 3.75, d (9.0) | | 3.80, d (9.0) | |
| 14 | | 71.1 | | 70.9 |
| 15a | 4.38, d (9.0) | 77.3 | 4.43, d (9.0) | 77.4 |
| 15b | 4.05, d (9.0) | | 4.02, d (9.0) | |
| 1' | | 170.7 | | 170.5 |
| 2' | | 111.4 | | 111.4 |
| 3' | | 149.2 | | 149.1 |
| 4' | 6.54, d (8.5) | 112.5 | 6.56, d (8.5) | 112.4 |
| 5' | 7.32, t (7.0) | 134.1 | 7.32, t (7.0) | 134.0 |
| 6' | 6.64, t (7.5) | 115.4 | 6.62, t (7.5) | 115.3 |
| 7' | 7.94, d (8.0) | 132.4 | 7.91, d (8.0) | 132.3 |

Experimental Example

BV-2 Microglial Cell Culture

BV-2 microglial cells were cultured in Dulbecco's modified Eagle medium supplemented with 5% Fetal bovine serum and 1% 100 units/mL of penicillin/streptomycin at 37° C. in a humidified 5% $CO_2$ incubator.

Experimental Example 1. Checking Cytotoxicities and NO Production Inhibiting Effects The BV-2 microglial cells seeded at a density of 1.25×10⁵ cell/each well in 24-well plate were pretreated with various concentration of compounds (12.5, 25, 50, and 100 μM for compounds 1-3 and 1, 2, 4, and 8 μM for compound 4) for 1 h, followed by LPS (200 ng/mL) for 24 h. 20 μL of MTT (2 mg/mL) solution was added to each well. After 1 h, the supernatant was sucked out and crystals of formazan were dissolved in DMSO. Optical density was measured at 550 nm using a microplate reader (Tecan Trading AG) and values were determined in comparison to control cells.

For Nitrite assay, the BV-2 microglial cells seeded at a density of $1.25 \times 10^5$ cell/each well in 24-well plate were pretreated with various concentrations of compounds 1-4 for 1 h, followed by LPS (200 ng/mL) for 24 h. A range of sodium nitrite dilutions was used to obtain a standard curve with the amount of nitrite in each sample. Absorbance was determined at 540 nm using a microplate reader (Tecan Trading AG).

Figure 9:
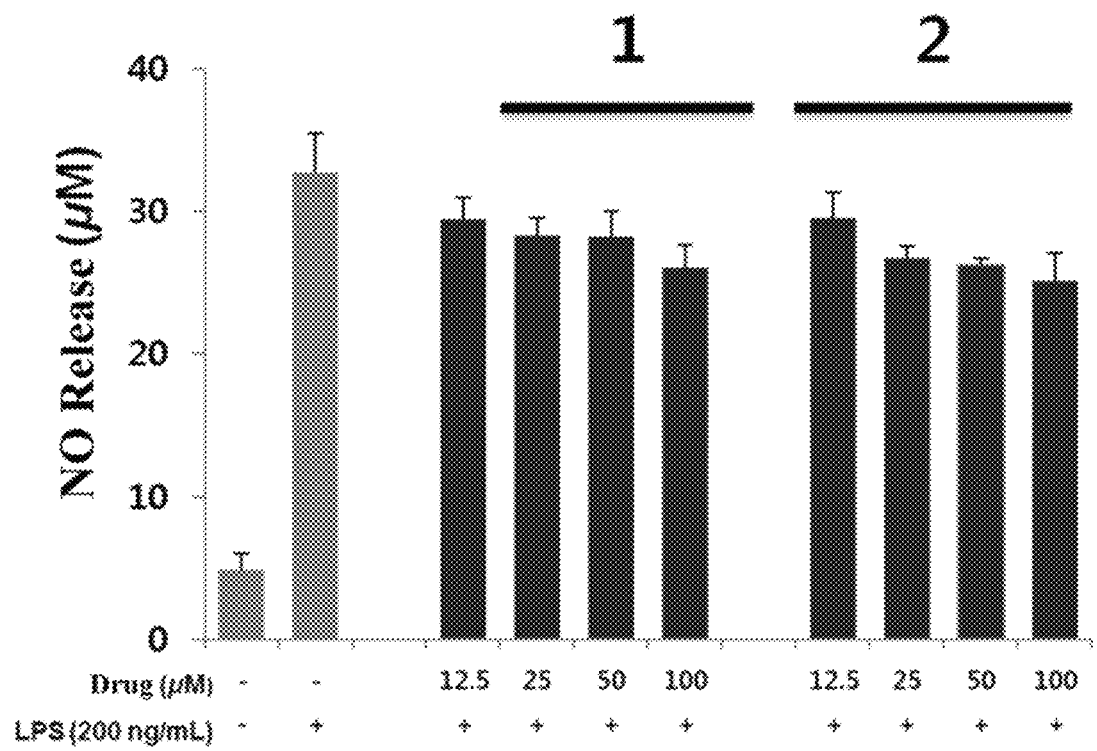
FIG. 9 shows effects of each of compounds 1 and 2 on LPS-stimulated NO production in BV-2 microglial cells. Line segments displayed in the middle of bar graphs denote standard deviations.
Figure 10:
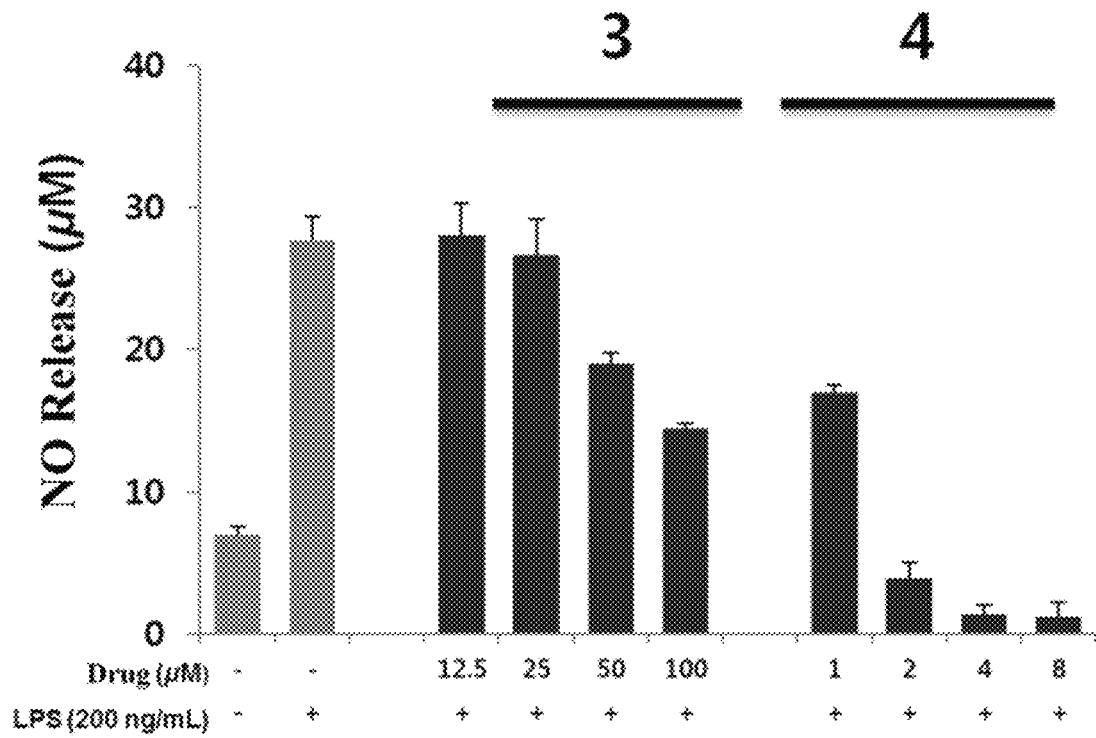
FIG. 10 shows effects of each of compounds 3 and 4 on LPS-stimulated NO production in BV-2 microglial cells. Line segments displayed in the middle of bar graphs denote standard deviations.
Figure 11:
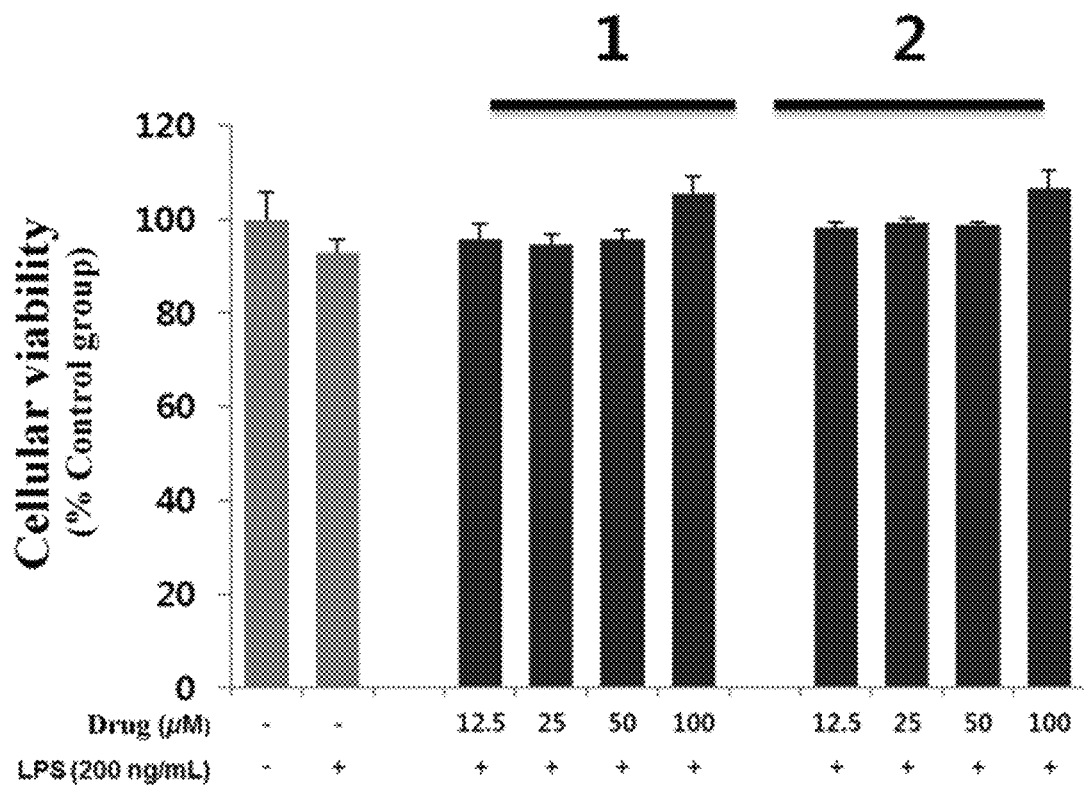
FIG. 11 shows effects of each of compounds 1 and 2 on LPS-stimulated cell viability in BV-2 microglial cells. Line segments displayed in the middle of bar graphs denote standard deviations.
Figure 12:
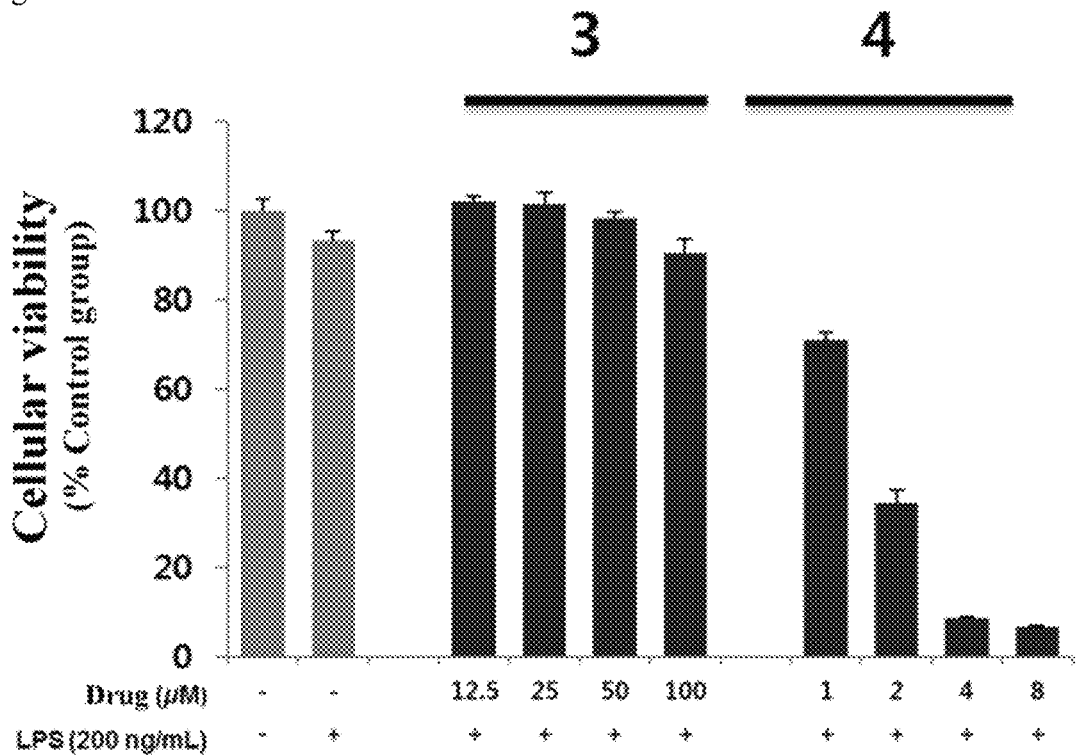
FIG. 12 shows effects of each of compounds 3 and 4 on LPS-stimulated cell viability in BV-2 microglial cells. Line segments displayed in the middle of bar graphs denote standard deviations.

As shown in FIGS. 9 and 10, an NO production was confirmed to be decreased by about 22% compared to the control group when treating BV-2 microglial cells with 100 μM of compound 1, and the NO production was indicated to be reduced by about 25% compared to the control group when treating the BV-2 microglial cells with 100 μM of compound 2. The NO production was found to be reduced by about 50% compared to the control group when treating the BV-2 microglial cells with 100 μM of compound 3, and the NO production was indicated to be reduced by about 93% compared to the control group although the BV-2 microglial cells were treated with the compound 4 having a low concentration of 1 to 8 μM. Although the BV-2 microglia indicated cellular viabilities similar to that of the control group when treating the BV-2 microglial cells with the compounds 1-3, the BV-2 microglial cells indicated a cellular viability of less than 80% when treating the BV-2 microglial cells with the compound 4. The compound 4 indicated a strong NO production inhibiting effect and cytotoxicity simultaneously when treating the BV-2 microglial cells with the compound 4 having a low concentration of less than 10 μM (FIG. 12).

Hereinabove, the present invention has been described through the Examples. It will be understood that the present invention can be implemented in the form of other specific form by those skilled in the art to which the present invention pertains without changing technical ideas or essential features of the present invention. Accordingly, the Examples described above are exemplary in all aspects and are understood not to be limited. The scope of the present invention is defined not by the detailed description thereof but by the scope of claims described later, and all modifications or modified forms derived from meanings and scope of the claims, and equivalent concepts thereof should be construed to be comprised in the scope of the present invention.

The invention claimed is:

1. A method of inhibition of NO production in lipopolysaccharide (LPS)-stimulated BV-2 microglial cells and inflammation generated in microglial cells in a subject, the method comprising administering to the subject in need thereof a therapeutically effective amount of a compound represented by the following Chemical Formula 1, an optical isomer, or a pharmaceutically acceptable salt thereof:

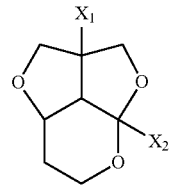

[Chemial Formula 1]

wherein:
$X_1$ is H or OR;
R is H or —Y—Z;
Y is carbonyl, amido, amide, $C_1$-$C_6$ alkyl, or $C_1$-$C_6$ alkylene;
Z does not exist, or is $C_5$-$C_{10}$ substituted or unsubstituted aryl, with the proviso that when Z is $C_5$-$C_{10}$ substituted aryl, the substituent is one or more selected from the group consisting of a hydroxy group, and $C_1$-$C_6$ alkyl and amino groups; and
$X_2$ is $C_3$-$C_{12}$ saturated or unsaturated linear or branched alkyl, or $C_3$-$C_{12}$ alkenyl;
wherein the compound inhibits NO production in microglial cells, thereby treating the neurodegenerative disease.

2. The method of claim 1, wherein the Y is carbonyl.

3. The method of claim 1, wherein the aryl is phenyl or naphthyl.

4. The method of claim 1, wherein the substituent is an amino group.

5. The method of claim 1, wherein the compound represented by Chemical Formula 1 is any one compound selected from the group consisting of Chemical Formulas 2, and 4 to 6:

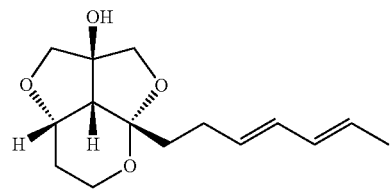

[Chemical Formula 2]

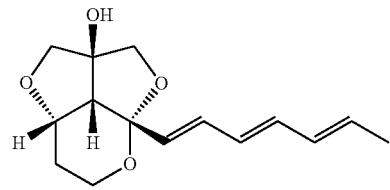

[Chemical Formula 4]

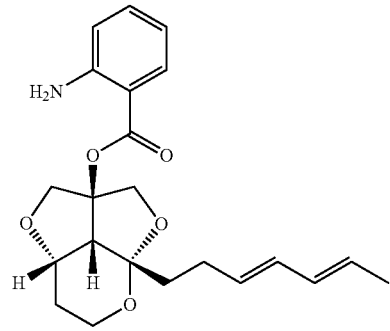

[Chemical Formula 5]

-continued
[Chemical Formula 6]
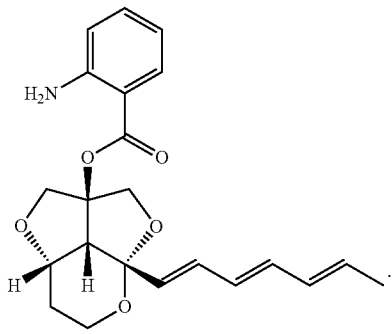
* * * * *